(12) United States Patent
Koudele et al.

(10) Patent No.: US 12,061,196 B2
(45) Date of Patent: Aug. 13, 2024

(54) METHOD FOR DETECTION AND INTERPRETATION OF RESULTS INDICATED ON A PHOTOGRAPHED DIAGNOSTIC TEST

(71) Applicant: MFB Fertility, Inc., Boulder, CO (US)

(72) Inventors: Larry Joseph Koudele, Erie, CO (US); Alexandra Marie Koudele, Boulder, CO (US)

(73) Assignee: MFB Fertility, Inc., Erie, CO (US)

( * ) Notice: Subject to any disclaimer, the term of this patent is extended or adjusted under 35 U.S.C. 154(b) by 360 days.

(21) Appl. No.: 17/522,696

(22) Filed: Nov. 9, 2021

(65) Prior Publication Data

US 2022/0146408 A1 May 12, 2022

Related U.S. Application Data

(60) Provisional application No. 63/112,051, filed on Nov. 10, 2020.

(51) Int. Cl.
*G06T 7/11* (2017.01)
*G01N 21/64* (2006.01)
(Continued)

(52) U.S. Cl.
CPC ... *G01N 33/54388* (2021.08); *G01N 21/6428* (2013.01); *G01N 33/689* (2013.01);
(Continued)

(58) Field of Classification Search
CPC .... G06T 7/11; G06T 7/90; G06T 2207/20132
See application file for complete search history.

(56) References Cited

U.S. PATENT DOCUMENTS

| 3,335,638 A | 8/1967 | John |
| 4,094,647 A | 6/1978 | Deutsch et al. |

(Continued)

FOREIGN PATENT DOCUMENTS

| CA | 3043270 A1 | 6/2018 |
| CN | 104697938 B | 4/2018 |

(Continued)

OTHER PUBLICATIONS

Bouchard et al., (2019). "Pilot Evaluation of a New Urine Progesterone Test to Confirm Ovulation in Women Using a Fertility Monitor," Front. Public Health, 7:184, 4 pages.
(Continued)

*Primary Examiner* — Kevin Ky
(74) *Attorney, Agent, or Firm* — MORRISON & FOERSTER LLP (57) ABSTRACT

An exemplary method of interpreting results indicated on a photographed diagnostic test comprises: sweeping the photographed diagnostic test, or cropped area of the photographed diagnostic test; creating a vector of color values including the color values obtained from a plurality of horizontal pixel positions on the photographed diagnostic test or cropped area of the photographed diagnostic test; identifying the location of the control line and each testing line depicted within the photographed diagnostic test; and calibrating to determine a hormone or analyte level corresponding to a color value of a test line. Systems of interpreting results indicated on a photographed diagnostic test are also provided.

13 Claims, 8 Drawing Sheets

Input Images 0.jpg
0 ug/Ml 1.jpg
3 ug/Ml (51) Int. Cl.
| | |
|---|---|
| *G01N 33/543* | (2006.01) |
| *G01N 33/68* | (2006.01) |
| *G01N 33/74* | (2006.01) |
| *G01N 33/76* | (2006.01) |
| *G06T 7/90* | (2017.01) |

(52) U.S. Cl.
CPC ............ *G01N 33/743* (2013.01); *G01N 33/76* (2013.01); *G06T 7/11* (2017.01); *G06T 7/90* (2017.01); *G06T 2207/20132* (2013.01)

(56) References Cited

U.S. PATENT DOCUMENTS

| | | | |
|---|---|---|---|
| 4,168,146 | A | 9/1979 | Grubb et al. |
| 4,235,601 | A | 11/1980 | Deutsch et al. |
| 4,361,537 | A | 11/1982 | Deutsch et al. |
| 4,376,110 | A | 3/1983 | David et al. |
| 4,450,239 | A | 5/1984 | Chatterton |
| 4,703,017 | A | 10/1987 | Campbell et al. |
| 4,775,636 | A | 10/1988 | Moeremans et al. |
| 4,855,240 | A | 8/1989 | Rosenstein et al. |
| 4,857,453 | A | 8/1989 | Ullman et al. |
| 4,861,711 | A | 8/1989 | Friesen et al. |
| 4,943,522 | A | 7/1990 | Eisinger et al. |
| 4,952,517 | A | 8/1990 | Bahar |
| 5,158,869 | A | 10/1992 | Pouletty et al. |
| 5,252,496 | A | 10/1993 | Kang et al. |
| 5,424,193 | A | 6/1995 | Pronovost et al. |
| 6,156,271 | A | 12/2000 | May |
| 6,319,676 | B1 | 11/2001 | Nazareth et al. |
| 6,352,862 | B1 | 3/2002 | Davis et al. |
| 6,451,619 | B1 | 9/2002 | Catt et al. |
| 6,699,722 | B2 | 3/2004 | Bauer et al. |
| 6,924,153 | B1 | 8/2005 | Boehringer et al. |
| 7,144,742 | B2 | 12/2006 | Boehringer et al. |
| 7,483,054 | B2 | 1/2009 | Lin et al. |
| 7,943,395 | B2 | 5/2011 | Wei et al. |
| 9,063,091 | B2 | 6/2015 | Tsai et al. |
| 9,206,254 | B2 | 12/2015 | Decourtye et al. |
| 9,386,221 | B2 | 7/2016 | Kauniskangas et al. |
| 9,787,815 | B2 | 10/2017 | Erickson et al. |
| 9,857,373 | B1 | 1/2018 | Pulitzer et al. |
| 9,939,385 | B2 | 4/2018 | Nazareth et al. |
| 11,029,321 | B2 | 6/2021 | Beckley |
| 11,061,026 | B2 | 7/2021 | Beckley |
| 11,131,665 | B1 | 9/2021 | Beckley |
| 11,855,659 | B2 * | 12/2023 | Nishikawa ............ H03M 3/462 |
| 2004/0253142 | A1 | 12/2004 | Brewster et al. |
| 2005/0130311 | A1 | 6/2005 | Coley et al. |
| 2006/0008896 | A1 | 1/2006 | Nazareth et al. |
| 2006/0121626 | A1 | 6/2006 | Imrich |
| 2009/0137478 | A1 | 5/2009 | Bernstein et al. |
| 2009/0228303 | A1 | 9/2009 | Faulkner et al. |
| 2010/0312137 | A1 | 12/2010 | Gilmour et al. |
| 2012/0038820 | A1 * | 2/2012 | Kempahonnaiah ...... A61B 5/00 348/370 |
| 2012/0040386 | A1 * | 2/2012 | Knappe ................ G01N 33/526 435/14 |
| 2012/0119984 | A1 * | 5/2012 | Sankarasubramaniam .................. G06V 40/50 382/165 |
| 2012/0197539 | A1 * | 8/2012 | Slupsky ............. G01R 33/4625 702/19 |
| 2012/0321519 | A1 | 12/2012 | Brown |
| 2013/0034908 | A1 * | 2/2013 | Barstis .................... G01N 21/78 436/124 |
| 2013/0065321 | A1 | 3/2013 | Nazareth et al. |
| 2013/0273563 | A1 | 10/2013 | Ehrenkranz |
| 2014/0051173 | A1 * | 2/2014 | Barstis ............... G01N 21/8483 422/403 |
| 2014/0147838 | A1 * | 5/2014 | Sempere ............. C12Q 1/6886 435/6.11 |
| 2014/0320677 | A1 * | 10/2014 | Jarvenpaa ............ G16H 30/40 382/128 |
| 2015/0032008 | A1 * | 1/2015 | Landesman .......... A61B 5/0084 600/476 |
| 2015/0057551 | A1 * | 2/2015 | Chou ................... A61B 5/1032 600/476 |
| 2015/0094227 | A1 | 4/2015 | McCarthy et al. |
| 2015/0109323 | A1 * | 4/2015 | Johnson ............... G06F 3/0488 345/594 |
| 2015/0304555 | A1 | 10/2015 | Ehrenkranz |
| 2015/0338387 | A1 | 11/2015 | Ehrenkranz |
| 2016/0139156 | A1 | 5/2016 | Lakdawala |
| 2016/0167042 | A1 | 6/2016 | Tyrrell et al. |
| 2016/0178607 | A1 | 6/2016 | Husheer et al. |
| 2016/0188937 | A1 | 6/2016 | Tyrrell et al. |
| 2016/0194718 | A1 * | 7/2016 | Lane ...................... A61K 31/55 435/6.12 |
| 2016/0210427 | A1 | 7/2016 | Mynhier et al. |
| 2016/0370389 | A1 * | 12/2016 | Barstis ............... G01N 21/8483 |
| 2017/0007215 | A1 | 1/2017 | Podoly |
| 2017/0011194 | A1 | 1/2017 | Arshad et al. |
| 2017/0327023 | A1 | 11/2017 | Leurck et al. |
| 2018/0088136 | A1 | 3/2018 | Saji et al. |
| 2018/0106799 | A1 | 4/2018 | Brenner et al. |
| 2018/0129722 | A1 | 5/2018 | Bormann et al. |
| 2018/0196037 | A1 | 7/2018 | Polwart et al. |
| 2018/0321251 | A1 | 11/2018 | Beckley |
| 2018/0366232 | A1 | 12/2018 | Dvorak et al. |
| 2019/0027251 | A1 * | 1/2019 | Pulitzer ................. G16H 30/40 |
| 2019/0073763 | A1 * | 3/2019 | Li ........................... G06F 18/22 |
| 2019/0212353 | A1 | 7/2019 | Yang et al. |
| 2019/0310576 | A1 * | 10/2019 | Tomii ................. G03G 15/0131 |
| 2019/0341127 | A1 * | 11/2019 | Lo ........................... G16B 40/00 |
| 2020/0078781 | A1 | 3/2020 | Beckley |
| 2020/0141953 | A1 | 5/2020 | Beckley |
| 2020/0141954 | A1 | 5/2020 | Beckley |
| 2020/0152038 | A1 | 5/2020 | Herbst et al. |
| 2021/0055310 | A1 | 2/2021 | Beckley |
| 2021/0231574 | A1 * | 7/2021 | Wang ..................... G01N 1/405 |
| 2021/0293800 | A1 | 9/2021 | Beckley |
| 2021/0293809 | A1 | 9/2021 | Beckley |
| 2021/0389311 | A1 | 12/2021 | Beckley |
| 2023/0248814 | A1 * | 8/2023 | Wu ..................... C07K 14/7051 424/186.1 |
| 2023/0374143 | A1 * | 11/2023 | Kjølby ................. A61K 31/41 |
| 2023/0408512 | A1 | 12/2023 | Beckley |
| 2024/0058805 | A1 | 2/2024 | Beckley |

FOREIGN PATENT DOCUMENTS

| | | |
|---|---|---|
| EP | 158746 A2 | 10/1985 |
| EP | 276152 A2 | 7/1988 |
| EP | 306772 A1 | 3/1989 |
| EP | 451800 A1 | 10/1991 |
| EP | 656118 B1 | 2/1997 |
| EP | 1066530 B1 | 11/2004 |
| EP | 2861991 B1 | 4/2015 |
| EP | 2839264 B1 | 7/2017 |
| EP | 2788764 B1 | 10/2017 |
| EP | 3052944 B1 | 8/2019 |
| GB | 2204398 B | 8/1991 |
| WO | WO-1994004924 A1 | 3/1994 |
| WO | WO-1995016920 A1 | 6/1995 |
| WO | WO-1998039657 A1 | 9/1998 |
| WO | WO-2006010072 A2 | 1/2006 |
| WO | WO-2007049157 A2 | 5/2007 |
| WO | WO-2013188860 A1 | 12/2013 |
| WO | WO-2015049510 A1 | 4/2015 |
| WO | WO-2016115608 A1 | 7/2016 |
| WO | WO-2016142610 A1 | 9/2016 |
| WO | WO-2016166415 A1 | 10/2016 |
| WO | WO-2017058827 A1 | 4/2017 |
| WO | WO-2017180909 A1 | 10/2017 |
| WO | WO-2017198204 A1 | 11/2017 |
| WO | WO-2018236792 A1 | 12/2018 |
| WO | WO-2019023926 A1 | 2/2019 |
| WO | WO-2019133920 A1 | 7/2019 |
| WO | WO-2019246361 A1 | 12/2019 |
| WO | WO-2021034412 A1 | 2/2021 |

(56) References Cited

FOREIGN PATENT DOCUMENTS

OTHER PUBLICATIONS

Ecochard et al., (2013). "Use of urinary pregnanediol 3-glucuronide to confirm ovulation," Steroids, 78:1035-1040.
Extended European Search Report and Written Opinion received for European Patent Application No. 18895132.1 mailed on Sep. 9, 2021, 12 pages.
Googleplay, (2015). "DaysyView" Valley Electronics, 5 pages.
Hermanson, (1996). "Chapter 20: Antibody Modification and Conjugation," Bioconjugate Techniques, pp. 783-823.
Indiegogo, (2017). "At Home Ovulation Double Check Test," available online at <https://www.indiegogo.com/projects/at-home-ovulation-double-check-test#/>, 14 pages.
International Search Rport and Written Opinion for International Patent Application No. PCT/US2021/72306 mailed on Feb. 3, 2022, 10 pages.
Kerrigan et al., (2001). "Comparison of ELISAs for Opiates, Methamphetamine, Cocaine Metabolite, Benzodiazepines, Phencyclidine, and Cannabinoids in Whole Blood and Urine," Clinical Chemistry, 47(3):540-547.
Koczula et al., (2016). "Lateral flow assays," Essays in Biochemistry, 60:111-120.
Leiva et al., (2019). "Pilot observational prospective cohort study on the use of a novel home-based urinary pregnanediol 3-glucuronide (PDG) test to confirm ovulation when used as adjunct to fertility awareness methods (FAMs) stage 1," BMJ Open, 9:e028496, 8 pages.
Maggio, (1980). "Chapter 3: Enzymes as Immunochemical Labels," Enzyme Immunoassay CRC Press, 54-70. Abstract Only.
Merriam-Webster, (2020). "Definition: base unit," Available online at <https://www.merriam-webster.com/dictionary/base unit>, 10 pages.
Mesen et al., (2015). "Progesterone and the Luteal Phase: A Requisite to Reproduction," Obstetrics and Gynecology Clinics of North America, 42(1):135-151, 19 pages.
MFB Fertility, Inc. (2017). "Ovulation Double Check, Catalog # MFB-01," retrieved online from <https://nebula.wsimg.com/9d9ad3495de83e7be3d53247867b8966?AccessKeyId=DA50EDF93F4AF80A8854&disposition=0&alloworigin=1>, 2 pages.
Munro et al., (1991). "Relationship of Serum Estradiol and Progesterone Concentrations to the Excretion Profiles of Their Major Urinary Metabolites as Measured by Enzyme Immunoassay and Radioimmunoassay," Clinical Chemistry, 37(6):838-844.
Pauillac et al., (1998). "An improved method for the production of antibodies to lipophilic carboxylic hapten using small amount of hapten-carrier conjugate," Journal of Immunological Methods, 220:105-114. Abstract Only.
PCT International Search Report with attached Written Opinion of the International Searching Authority for International Application No. PCT/US2018/68027, dated Mar. 26, 2019, 16 pages.
PCT International Search Report with attached Written Opinion of the International Searching Authority for International Application No. PCT/US2020/40600, dated Nov. 20, 2020, 13 pages.
Santoro et al., (2012). "Reproductive Hormones and the Menopause Transition," Obstet Gynecol Clin North Am., Author manuscript available online at <https://www.ncbi.nlm.nih.gov/pmc/articles/PMC3197715/>, 15 pages.
Su et al., (2013). "Hormone changes associated with the menopausal transition," Minerva Ginecol., Author manuscript available online at <https://www.ncbi.nlm.nih.gov/pmc/articles/PMC3823936/>, 9 pages.
Su et al., (2017). "Detection of ovulation, a review of currently available methods," Bioeng Transl Med., 16:238-246.
Unpublished U.S. Appl. No. 17/522,696, filed Nov. 9, 2021 titled "Method for Detection and Interpretation of Results Indicated on a Photographed Diagnostic Test," (Copy not submitted herewith pursuant to the waiver of 37 C.F.R. § 1.98(a)(2)(iii)).
Unpublished U.S. Appl. No. 17/636,755, filed Jul. 2, 2020 titled "Systems and Methods for Menstrual Cycle Testing," (Copy not submitted herewith pursuant to the waiver of 37 C.F.R. § 1.98(a)(2)(iii)).
Vyjayanthi et al., (1995). "Binding characteristics of bovine serum albumin-afloxin B1 to polystyrene microtiter plates: Importance of hapten to carrier protein molar ratio," Indian Journal of Experimental Biology, 33:329-332. Abstract Only.
Youtube, (2017). "How do Ovulation Double Check Tests work," Available online at <https://www.youtube.com/watch?v=HX-yNp>, 1 page.
Youtube, (2018). "Testing progesterone at home: MFB Proof test," Available online at <https://m.youtube.com/watch?v=zjMR9FDQip0>, 1 page.
Edwards et al., (2003). "The remarkable flexibility of the human antibody repertoire; isolation of over one thousand different antibodies to a single protein, BlyS," Journal of Molecular Biology, 334: 103-118.
Goel et al., (2004). "Plasticity within the Antigen Combining Site May Manifest as Molecular Mimicry in the Humoral Immune Response," The Journal of Immunology, 173(12):7358-7367.
Lloyd et al., (2009). "Modelling the human immune response: performance of a 1011 human antibody repertoire against a broad panel of therapeutically relevant antigens," Protein Engineering, Design & Selection, 22(3):159-168.
Unpublished U.S. Appl. No. 18/696,892, filed Mar. 8, 2024 titled "Devices, Systems and Methods for Detection of Beta Subunit of Luteinizing Hormone," (Copy not submitted herewith pursuant to the waiver of 37 C.F.R. § 1.98(a)(2)(iii)).

* cited by examiner

FIG. 1A
0.jpg
0 ug/Ml

FIG. 1B
1.jpg
3 ug/Ml

FIG. 1C
10.jpg
10 ug/mL

Input Images

Filtered and Averaged Multi-Sample Data Plots (shown with normalized values)

METHOD FOR DETECTION AND INTERPRETATION OF RESULTS INDICATED ON A PHOTOGRAPHED DIAGNOSTIC TEST

CROSS-REFERENCE TO RELATED APPLICATION

This application claims the priority to and benefit of U.S. Provisional Application 63/112,051 filed on Nov. 10, 2020, the entire content of which is incorporated herein by reference for all purposes.

BACKGROUND

A variety of diagnostic tests, particularly lateral flow assay tests of various types, purport to provide a visual indication in a testing zone following the application of a fluid. Such diagnostic tests typically operate by associating a result with the presence or absence or color, optionally in association with a labelling element such as colloidal gold or colored latex, within a testing zone. Exemplary diagnostic tests are described in the following U.S. patent applications: Ser. No. 15/900,794 filed on Feb. 20, 2018; Ser. No. 15/974,229 filed on May 2, 2018; Ser. No. 16/381,229 filed on Apr. 11, 2019; Ser. No. 16/544,554 filed on Aug. 19, 2019; Ser. No. 16/732,766 filed on Jan. 2, 2020; and Ser. No. 16/732,823 filed on Jan. 2, 2020, each of which is hereby incorporated by reference in their entirety with priority claimed thereto. Exemplary diagnostic tests are also described in International (PCT) Patent Application PCT/US18/68027 filed on Dec. 28, 2018 hereby incorporated by reference in its entirety with priority claimed thereto.

A number of challenges remain associated with the interpretation of diagnostic tests. For example, it remains a challenge to determine the location and/or result of a testing line on a diagnostic test. This challenge is often associated with the interpretation of a digital photograph of such a diagnostic test. The challenge is exacerbated when the absence of a line within a testing zone indicates a positive result, or the presence of a line indicates a negative result. The challenge also remains in association with quantitative interpretations of an amount of hormone or analyte within the applied fluid as correlated to a color or color intensity displayed on the diagnostic test.

Further, variations associated with the color, brightness, camera variations and other variables associated with photography of the test remain. For example, the detected color values associated with a photographed diagnostic test in one lighting condition may dramatically differ from the photographed diagnostic test in another lighting condition. Similarly, camera variations and other variables can dramatically affect the detected color values associated with the strip. This challenge is particularly acute when attempting to measure the RGB color value associated with most predominant color within a testing zone associated with the result indicated on a photographed diagnostic test. Therefore, the interpretation of such a photographed diagnostic test, whether associated with the detection of a binary positive/negative result for one or a plurality of hormone(s) or analyte(s), or the determination of a quantitative measurement of one or a plurality of hormone(s) or analyte(s) within a fluid applied to the diagnostic test, remains an unmet challenge.

BRIEF SUMMARY

In some aspects, provided is a method of interpreting results indicated on a photographed diagnostic test. In some embodiments, the method comprises: sweeping the photographed diagnostic test, or cropped area of the photographed diagnostic test; creating a vector of color values including the color values obtained from a plurality of horizontal pixel positions on the photographed diagnostic test or cropped area of the photographed diagnostic test; identifying the location of the control line and each testing line depicted within the photographed diagnostic test; and calibrating to determine a hormone or analyte level corresponding to a color value of a test line.

In some embodiments, the method further comprises: calculating the average of color channel values from a plurality of vertical pixel positions at a particular horizontal pixel position of the photographed diagnostic test or cropped area of the photographed diagnostic test; and repeating the calculating the average step to obtain the average of color channel values from a plurality of vertical pixel positions for each of a plurality of horizontal pixel positions.

In some embodiments, the method further comprises: filtering the photographed diagnostic test or the cropped area of the photographed diagnostic test.

In some embodiments, the method further comprises: normalizing the depth of the control line.

In some embodiments, the normalizing further comprises: determining the normalization factor; and multiplying each of the values collected at each of the horizontal pixel positions by the normalization factor.

In some embodiments, the calibration further comprises: holding constant the environmental conditions of each photographed diagnostic test throughout the calibration to minimize the impact of environmental factors.

In some embodiments, the calibration further comprises: photographing each diagnostic test during calibration at a consistent time period from the application of a fluid containing a hormone or analyte subject to evaluation.

In some embodiments, the diagnostic test comprises a single testing zone configured to indicate the concentration of a hormone or analyte in a fluid applied to the diagnostic test.

In some embodiments, the diagnostic test comprises a plurality of testing zones each configured to indicate the concentration of a discrete hormone or analyte in a fluid applied to the diagnostic test.

In some embodiments, the color values of a RGB channel other than the predominant color are expected on at least one test line of the photographed diagnostic test.

In some embodiments, the method further comprises: converting a color image to a grayscale image prior to the creating a vector of color values step.

In some embodiments, the method further comprises: converting a grayscale image to a RGB image.

In other aspects, provided is a system of interpreting results indicated on a photographed diagnostic test. In some embodiments, the system comprises: one or more processors; a memory; and one or more programs, wherein the one or more programs are stored in the memory and configured to be executed by the one or more processors, the one or more programs including instructions for: sweeping the photographed diagnostic test, or cropped area of the photographed diagnostic test; creating a vector of color values including the color values obtained from a plurality of horizontal pixel positions on the photographed diagnostic test or cropped area of the photographed diagnostic test; identifying the location of the control line and each testing line depicted within the photographed diagnostic test; and calibrating to determine a hormone or analyte level corresponding to a color value of a test line.

In yet other aspects, provided is a non-transitory computer-readable storage medium stores one or more programs. In some embodiments, the one or more programs comprise instructions, which when executed by one or more processors of an electronic device having a display, cause the electronic device to: sweep the photographed diagnostic test, or cropped area of the photographed diagnostic test; create a vector of color values including the color values obtained from a plurality of horizontal pixel positions on the photographed diagnostic test or cropped area of the photographed diagnostic test; identify the location of the control line and each testing line depicted within the photographed diagnostic test; and calibrate to determine a hormone or analyte level corresponding to a color value of a test line.

DESCRIPTION OF THE FIGURES

The present application can be understood by reference to the following description taken in conjunction with the accompanying figures.

FIGS. 1A-C generally depict neutral light calibration test strip photos. Each of these were taken 10 minutes after processing. Each photographed strip is a calibration strip dipped in a synthetic urine solutions of varying hormone or analyte amounts, timed and then photographed. The photographs show that the color intensity of the testing line changes with the changing amount of hormone or analyte amount, while the color intensity of the control line stays generally constant with the changing hormone or analyte amount. The file name associated with each photograph corresponds with the numerical amount in ug/mL to facilitate ease of understanding and utilization in the context of the methods described herein.

FIGS. 2A-2B generally depict a plot comparison of normalized vs. un-normalized averaged and filtered Data. These figures demonstrate that the shape of the depicted graph does not change though each of the values of the locations on the graph associated with the test line, control line, and midpoint (a location outside of the test line and control line area) change.

FIGS. 3A-C generally depict a comparison of raw single sweep data points. These graphs each depict a graph of one sweep (depicted by the red dotted line across the photograph of the diagnostic test) showing the unchanged RGB channel color values detected at a plurality of horizontal pixel positions across the photographed diagnostic test moving in a left to right direction.

FIGS. 4A-C generally depict a comparison of filtered single sweep data points. These graphs each depict a graph of one sweep (depicted by the red solid line across the photograph of the diagnostic test) showing the RGB channel color values following the application of a filter, optionally a digital low pass filter, detected at a plurality of horizontal pixel positions across the photographed diagnostic test moving in a left to right direction.

FIGS. 5A-C generally depict a comparison of filtered & averaged multiple-sample data points. These graphs each depict a graph of the average RGB channel color value of multiple sweeps (each sweep depicted by a red solid line across the photograph of the diagnostic test), the average RGB channel color value of the sweeps calculated at each horizontal pixel location across the image from left to right following the application of a filter, optionally a digital low pass filter. Each graph depicts normalized value, where a normalization factor is determined by calculating for the coefficient needed to multiply the raw control line value to arrive at a value of 75.0, and then multiplying the test line and midpoint values by the coefficient to determine the normalized values.

FIG. 6B depicts results of analysis of FIG. 6A (e.g., output from analysis script). Twenty one-pixel-high RGB color samples across the length of the image ("sweeps") are highlighted in red (i.e., the horizontal lines); control line detection is indicated by line 608; other line detections are indicated by lines 602, 604, and 606.

FIG. 6C. Output plot from test strip analysis. The plot marks the control line detection and the test line detections. The inner regions of interest as determined by control line (rightmost line) and LH line (leftmost line) detections are highlighted, including the PdG line region and the E1G line region. Additionally, ends of edge shadows (edges of valid analysis window) and midpoints (blank area samples used for relative intensity measurements) are marked. Data is normalized and the rounded measurements are printed.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

The present disclosure relates to a method to determine the result or plurality of results indicated by a photographed diagnostic test. There is a need to normalize the color value detected via a photographed diagnostic test and accurately determine the result or plurality of results. In a preferred embodiment, this is accomplished via a measurement of the normalized color intensity or value of each test line on the photographed diagnostic test via evaluation of a RGB color channel.

In a preferred embodiment, the chosen RGB color channel corresponds to a color other than the predominant color indicated or expected in the testing zone of the photographed diagnostic test. For example, in the example where the predominant color associated with at least one test line or a plurality of test lines (and optionally the control line) of a photographed diagnostic test is red, the appropriate RGB color channel to measure, normalize and average is the green color channel, not the red color channel. For instance, an evaluation of the green color channel gives a highly accurate indication of the magnitude of the red color associated with testing zone of the photographed diagnostic test. In this example, therefore, it is advantageous to analyze the green color channel because the diagnostic test predominantly displays red color to indicate the presence or absence of a tested hormone or analyte within the testing zone, in an example due to the choice of colloidal gold as the labeling material. In other examples, it is advantageous to analyze any color channel or combination of color channels predominantly excluding the color channel pertaining to the predominantly displayed color within each test line depicted within a photograph of a particular diagnostic test. Therefore, the color channel to evaluate in association with the collected color values as described herein is of a RGB channel other than the predominant color expected on at least one test line of the photographed diagnostic test.

In various embodiments, the choice of color channel or combinations of any set of color channels for evaluation could differ depending upon the predominantly displayed color or hue appearing within one test line or a plurality of test lines. In a preferred embodiment, the color of label displayed within a test line is predominantly and/or generally red to indicate the absence of the targeted hormone or analyte. It has therefore been determined in such example that it is advantageous to provide an accurate indication via the measurement of the RGB green color channel. In other examples, such as that the example where the color displayed within the testing zone predominantly exhibits a blue hue, it may be preferable to measure, average and normalize the values associated with the RGB red color channel to provide an indication of the magnitude of the blue coloration and corresponding hormone or analyte levels in the applied sample.

In an alternative embodiment, it is advantageous to analyze shades of gray when the color of the pigment, for example in correlation with a concentration of hormone and/or analyte, is difficult to anticipate. One skilled in the art would recognize that by utilizing color values associated with shades of gray (i.e. grayscale color values), the RGB values would be equal. In such example, there is advantage to first converting a color (RGB or alternative color) image to a grayscale image prior to the creating a vector of color values step described herein. It may be further advantageous in association with the method described herein, optionally following the converting the color image step or optionally where the photographed diagnostic test has otherwise been stored in grayscale, to perform the step of converting the grayscale image to a RGB color image where the red, green and blue channels have equal values. In such case any of the red, green and/or blue channels may be selected to perform the analysis in association with the teachings herein with equal effect, as in such circumstance a color's three red/green/blue numbers would be equal.

Figure 1A:
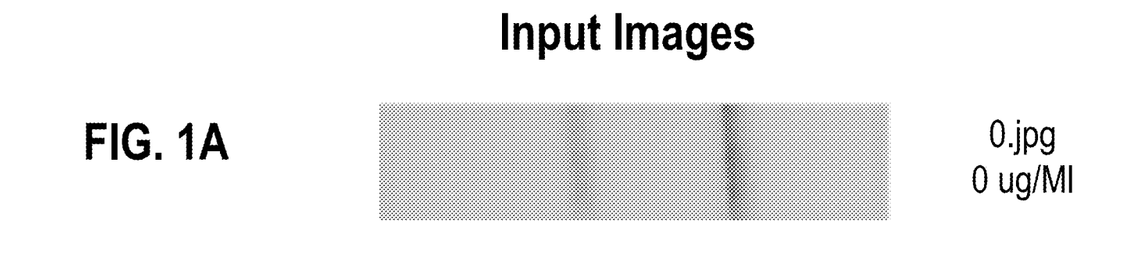
FIG. 1A depicts a photo named 0.jpg. This calibration strip was photographed 10 minutes after being applied with a synthetic urine solution containing 0 ug/mL of a hormone or analyte amount.
Figure 1B:
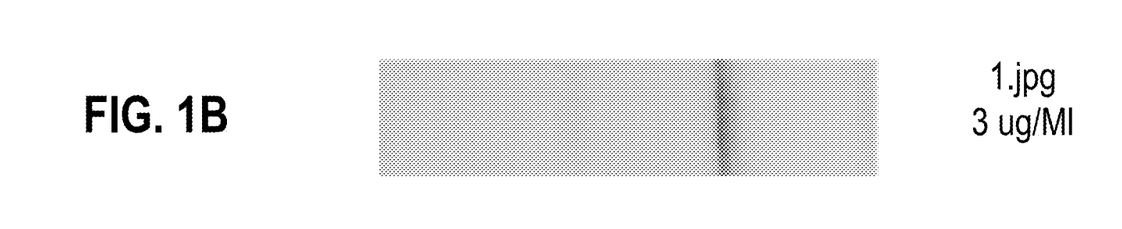
FIG. 1B depicts a photo named 3.jpg. This calibration strip was photographed 10 minutes after being applied with a synthetic urine solution containing 3 ug/mL of a hormone or analyte amount.
Figure 1C:
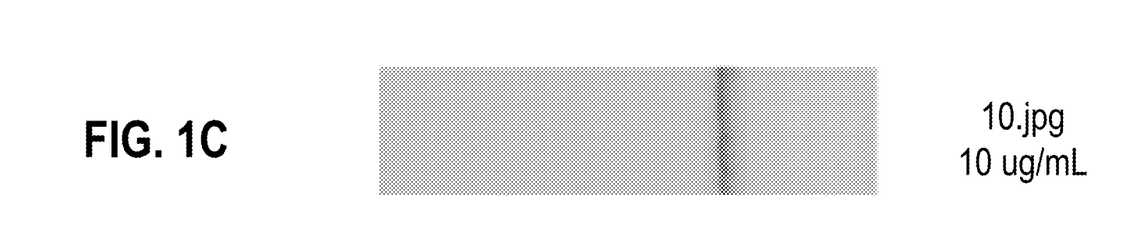
FIG. 1C depicts a photo named 10.jpg. This calibration strip was photographed 10 minutes after being applied with a synthetic urine solution containing 10 ug/mL of a hormone or analyte amount.
Figure 2A:
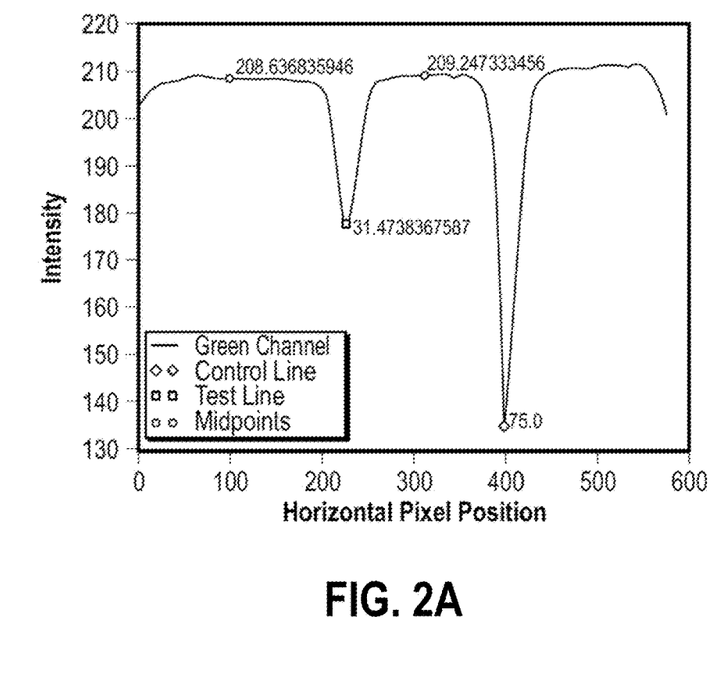
FIG. 2A depicts the normalized data, normalizing the RGB channel color values detected at the midpoints and test line of the diagnostic test to the control line of the diagnostic test set at a value of 75.
Figure 2B:
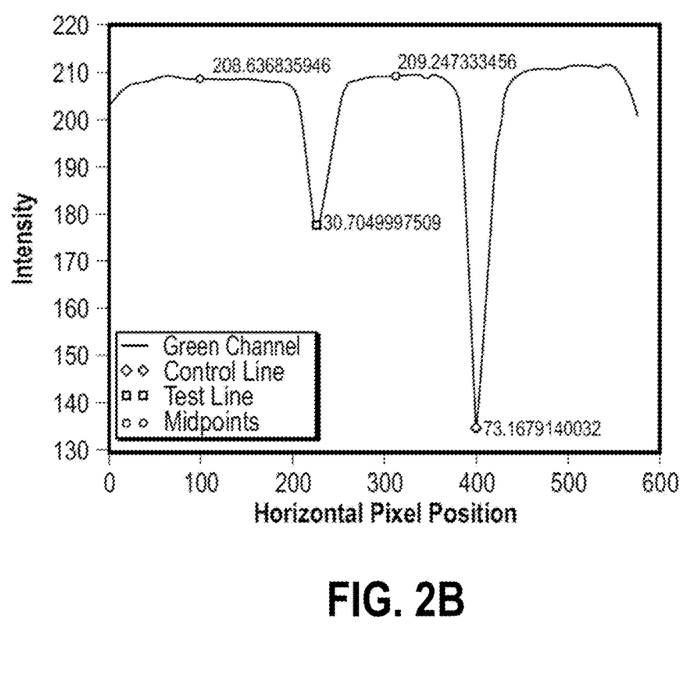
FIG. 2B depicts the un-normalized data, depicting the raw, unchanged RGB channel color values detected at the midpoints, test line and the control line of the diagnostic test.

Embodiments of the present disclosure incorporate a plurality of steps in association with a digital photograph of a diagnostic test. In various examples, it may be preferable to crop a portion of the photograph of the diagnostic test, for instance to the exemplary areas depicted in FIGS. 1A-1C, in particular to exclusively capture the testing window of the photographed diagnostic test comprising one or more test lines and a control line. In a preferred embodiment, the control line of a photographed diagnostic test appears as the rightmost line appearing within a test window region of the diagnostic test. In some embodiments, the steps comprise:

1. Sweeping the Photograph, or Cropped Area of a Photograph, of a Diagnostic test.

In various embodiments, the photograph of a diagnostic test in association with the method steps described herein is captured and stored digitally in association with a computing device, optionally a smartphone. In a preferred embodiment, a plurality of sweeps are performed along the whole length of the area of the photograph of the diagnostic test, or cropped area of the photograph. In an example, the sweeps are depicted on FIGS. 5A-5C as a red horizontal line. In one embodiment, 20 sweeps are performed through the whole length of the cropped portion of the strip, corresponding to 3 pixels apart vertically. The number of sweeps may vary in varying embodiments to account for the processing time needed to collect each value and/or the level of precision desired associated with the collected sample, for example. The sweeping step is important, as during each sweep a different set of pixels, a different amount of noise, different phase of noise, and different amplitude of noise is detected, and it is useful to average or normalize values to arrive at values corresponding to an improved interpretation of the diagnostic test. During the sweeping step in a preferred embodiment, a programmatic script is configured to sweep across the length of the image horizontally to take a sample. During each sweep, a RGB color channel intensity, optionally the RGB green color channel intensity, is recorded (each intensity value occurring on integer scale of 0-255) in association with a plurality of horizontal pixel positions. Optionally, following averaging, normalization, and/or filtering, decimal values are then included to enhance precision. In varying embodiments, the sweeping step may be performed on a photograph of a diagnostic test comprising a single testing zone or a photograph of a diagnostic test comprising a plurality of testing zones.

2. Calculating the Average of Color Channel Intensities of a Plurality of Vertical Pixel Positions, at Each of a Plurality of Horizontal Pixel Positions of the Photograph or Cropped Area of a Photograph of a Diagnostic Test.

It is advantageous to reduce the noise associated with a photograph of a diagnostic test. In an example of use, noise—or the variation of color values along the vertical axis at each of a plurality of horizontal positions—detrimentally impacts the accuracy of the result depicted on a diagnostic test. In preferred embodiment, the detrimental effect associated with noise may be significantly reduced by averaging the plurality of RGB color channel values collected during the sweeping step along the vertical axis located at each of a plurality of pixel positions along the horizontal length of the photographed diagnostic test. In an embodiment, multiple samples are taken from the photograph or area of a digital photograph of a diagnostic test spaced out evenly along the vertical axis at each of a plurality of positions along the horizontal axis of the photograph or cropped area of the photograph. Therefore, in an embodiment it is advantageous to additionally perform one or more steps of repeating the calculating the average step to obtain the average of color channel values from a plurality of vertical pixel positions for each of a plurality of horizontal pixel positions. In varying embodiments, the calculating step may be performed on a photograph of a diagnostic test comprising a single testing zone or a photograph of a diagnostic test comprising a plurality of testing zones.

3. Creating a Vector of Color Values Including the Color Values Obtained from a Plurality of Horizontal Pixel Positions on the Photograph or Cropped Area of the Photograph.

Figure 5A:
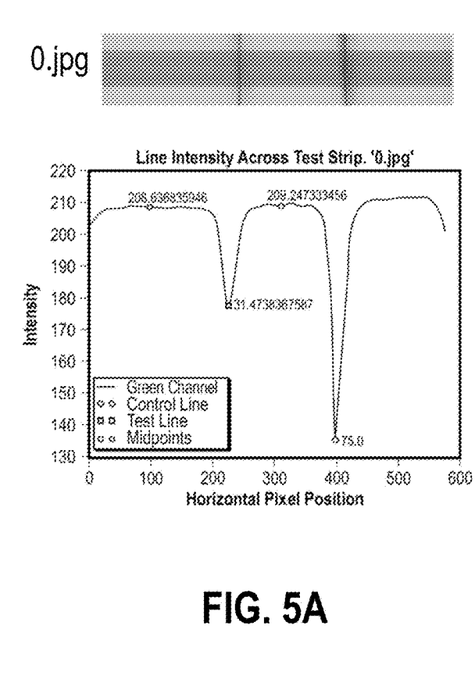
FIG. 5A depicts the average of the exemplary detected RGB channel color values following the application of a filter, optionally a digital low pass filter, at each horizontal pixel location moving from right to left across the photograph of the diagnostic test, following the application to the diagnostic test of a synthetic urine solution containing 0 ug/mL of a hormone or analyte amount (and correspondingly named 0.jpg) moving in a left to right direction. Note that the red associated with the test line is clearly visible at the location of the test line both on the photographed diagnostic test and as indicated on the graph, corresponding to a clearly identifiable dip in the average detected green RGB color value at a horizontal pixel position range of approximately 210-230 as depicted on the graph.
Figure 5B:
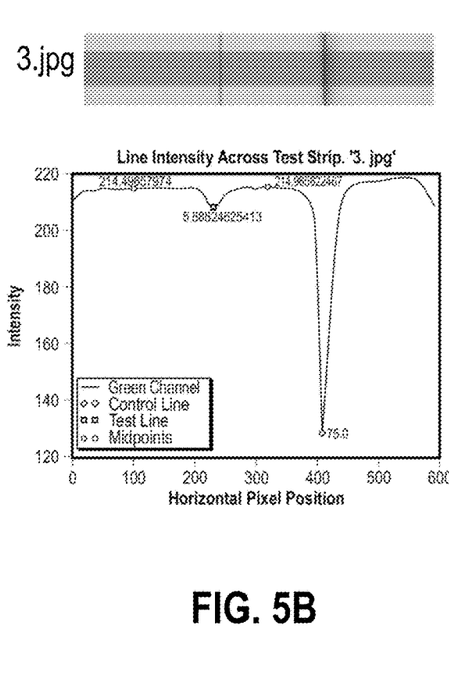
FIG. 5B depicts the average of the exemplary detected RGB channel color values following the application of a filter, optionally a digital low pass filter, at each horizontal pixel location moving from right to left across the photograph of the diagnostic test, following the application to the diagnostic test of a synthetic urine solution containing 3 ug/mL of a hormone or analyte amount (and correspondingly named 3.jpg) moving in a left to right direction. Note that the red associated with the test line is clearly visible at the location of the test line both on the photographed diagnostic test and as indicated on the graph, corresponding to a clearly identifiable dip in the average detected green RGB color value at a horizontal pixel position range of approximately 210-230 as depicted on the graph.
Figure 5C:
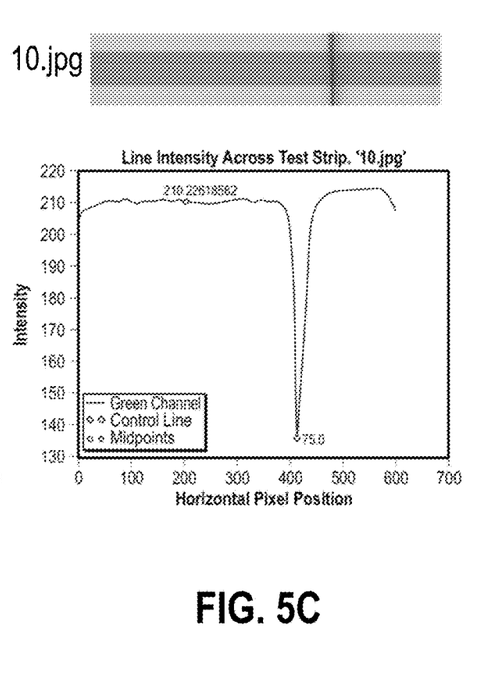
FIG. 5C depicts the average of the exemplary detected RGB channel color values following the application of a filter, optionally a digital low pass filter, at each horizontal pixel location moving from right to left across the photograph of the diagnostic test, following the application to the diagnostic test of a synthetic urine solution containing 10 ug/mL of a hormone or analyte amount (and correspondingly named 10.jpg) moving in a left to right direction. Note that the red associated with the test line is clearly not visible at the location of the test line both on the photographed diagnostic test and as indicated on the graph, corresponding to no identifiable dip in the average detected green RGB color value at a horizontal pixel position range of approximately 210-230 as depicted on the graph.
Figure 6A:
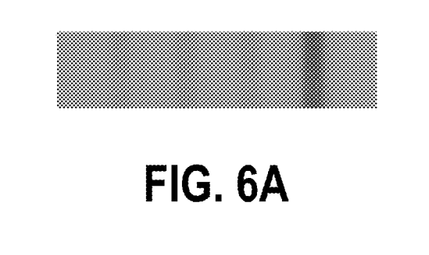
FIG. 6A depicts a typical test strip window input image. This example represents a test dipped in a fluid with known concentration of 2.5 ug per ml of PdG.
Figure 6B:
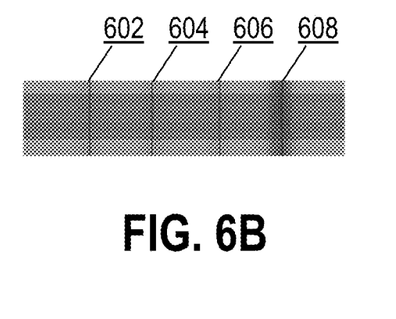
Figure 6C:
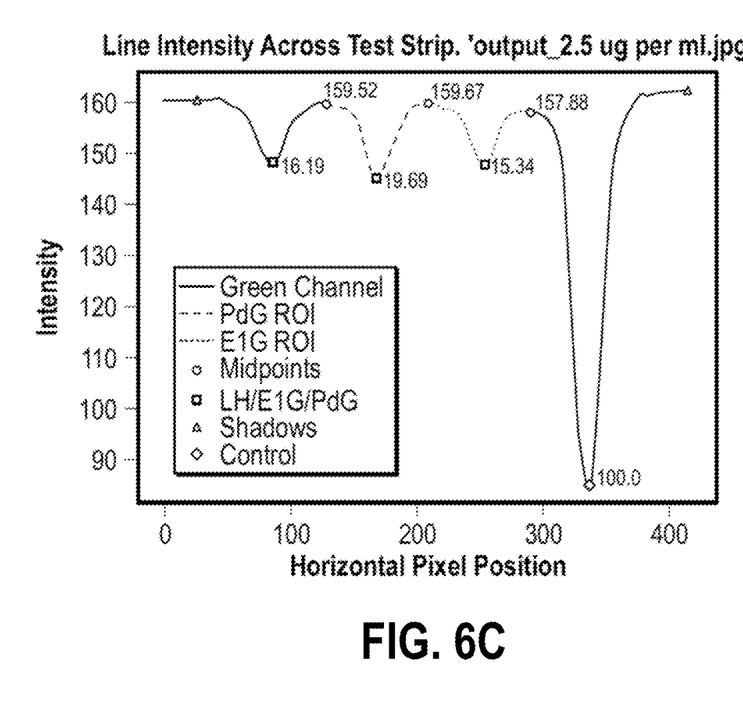
Figure 7A:
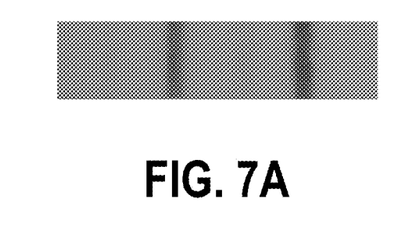
FIGS. 7A-C demonstrate a similar analysis of a strip (100 ng per ml of E1G) wherein shadow detection narrowed the valid window for analysis. Determined by the ends of edge shadows markers, the edge of the valid analysis window on the left side begins farther to the right than in the previous example, due to the measured drop in intensity on that side.
Figure 7B:
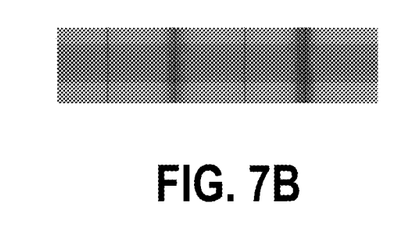
Figure 7C:
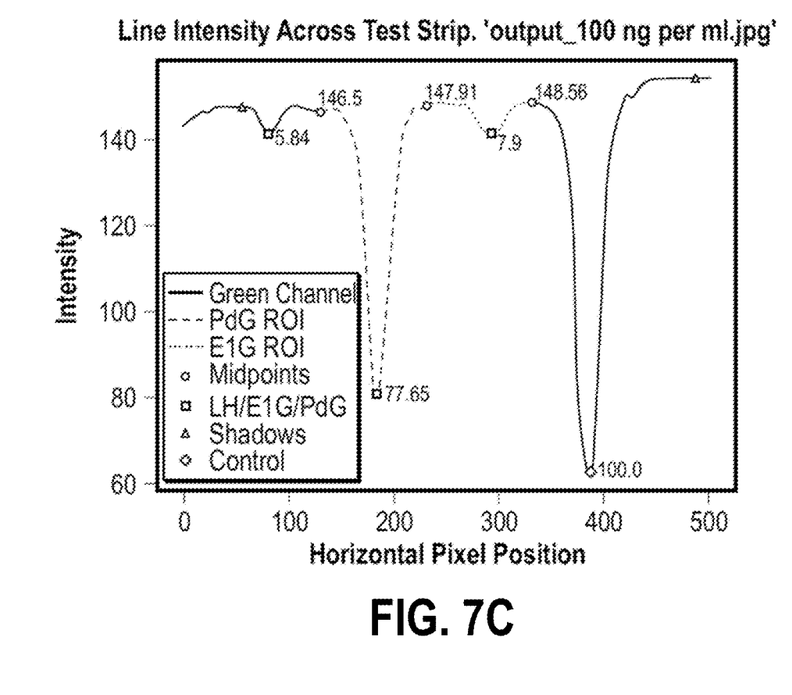

During the creating a vector step, a single array vector consisting of a plurality of values, each of the plurality of values corresponding to the RGB color channel value associated with a discrete horizontal pixel position on the photograph or cropped area of a photograph of a diagnostic test, is created. In an embodiment in which the calculating the average step is performed, each of the plurality of values corresponds to the average of RGB color channel values from a plurality of vertical pixel positions at a horizontal pixel position on the photograph or cropped area of the photograph. In a preferred embodiment, the plurality of values consists of the RGB green color channel numerical values. In alternative embodiments, however, any of the RGB values may be chosen, or a combination of them with different multipliers may be chosen, to create the vector of values. As depicted in FIGS. 5A-5C, for example, considering the magnitude of the RGB green color value as a function of the x axis, as the horizontal pixel position approaches and enters a red region (in the example possibly corresponding to the testing line or always corresponding to the control line), the RGB green color channel value dips. In varying embodiments, the creating the vector step is performed on a photograph of a diagnostic test comprising a single testing zone or a photograph of a diagnostic test comprising a plurality of testing zones.

4. Filtering the Photograph or the Cropped Area of the Photograph.

During this filtering step, a digital low pass filter (DSP or digital signal process) is applied to optimize or minimize the amount of noise associated with the digital photograph or cropped area of the digital photograph without affecting the amplitude significantly. In an embodiment, the filtering step is applied to the plurality of averages of RGB color channel values. In one example, a single pole recursive IIR low pass filter is utilized. For purposes associated with interpreting the result indicated on a diagnostic test, the single pole recursive IIR low pass filter works sufficiently to smooth out and reduce the noise of associated with the digital photograph or cropped area of the digital photograph of a diagnostic test. As a result, accurate and repeatable measurements on the depth of the amplitude of the color indicated may be made. In other examples recursive IIR (infinite impulse response filter) and non-recursive FIR (finite response filter) filters may be applied.

Figure 3A:
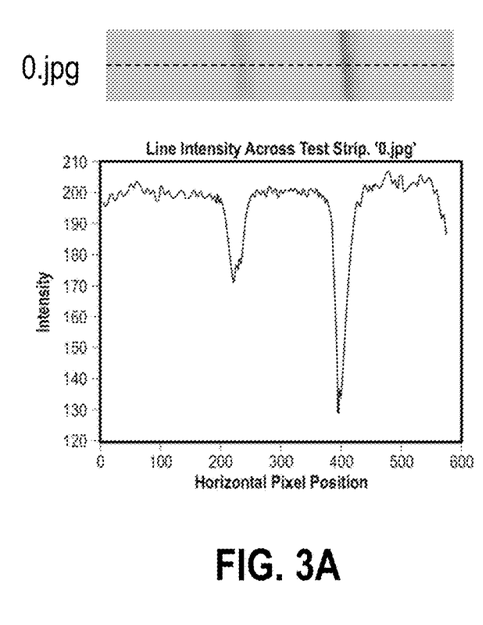
FIG. 3A depicts the raw detected RGB channel color values detected at a plurality of horizontal pixel positions across the photographed diagnostic test following the application of a synthetic urine solution containing 0 ug/mL of a hormone or analyte amount (and correspondingly named 0.jpg) moving in a left to right direction. Note that the red associated with the test line is clearly visible at the location of the test line both on the photographed diagnostic test and as indicated on the graph, corresponding to a clearly identifiable dip in the detected green RGB color value at a horizontal pixel position range of approximately 210-230 as depicted on the graph.
Figure 3B:
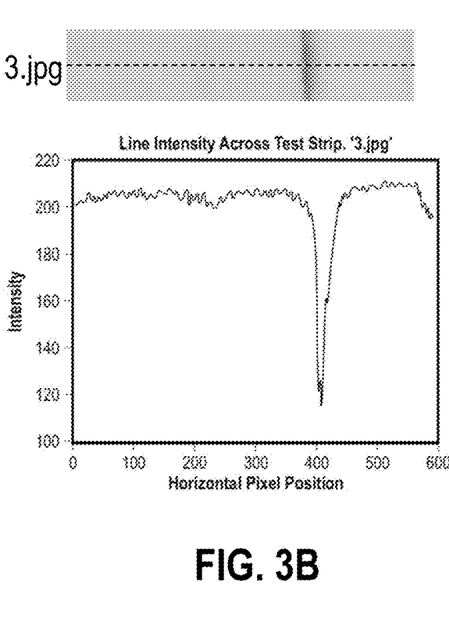
FIG. 3B depicts the raw detected RGB channel color values detected at a plurality of horizontal pixel positions across the photographed diagnostic test following the application of a synthetic urine solution containing 3 ug/mL of a hormone or analyte amount (and correspondingly named 3.jpg) moving in a left to right direction. Note that the red associated with the test line is only very slightly visible at the location of the test line both on the photographed diagnostic test and as indicated on the graph, corresponding to an only slightly identifiable dip in the detected green RGB color value at a horizontal pixel position range of approximately 210-230 as depicted on the graph.
Figure 3C:
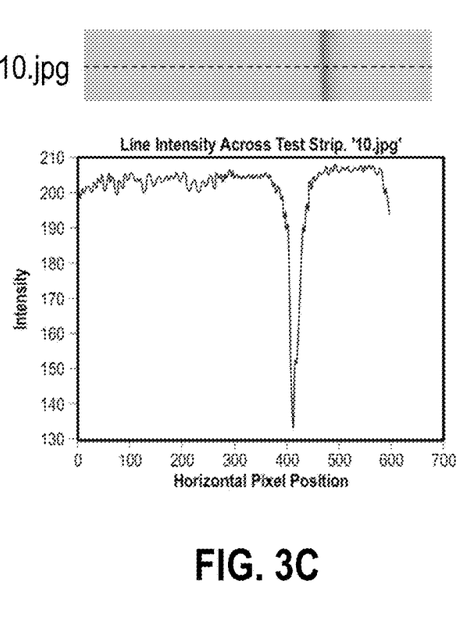
FIG. 3C depicts the raw detected RGB channel color values detected at a plurality of horizontal pixel positions across the photographed diagnostic test following the application of a synthetic urine solution containing 10 ug/mL of a hormone or analyte amount (and correspondingly named 10.jpg) moving in a left to right direction. Note that the red associated with the test line is not visible at the location of the test line both on the photographed diagnostic test and as indicated on the graph, corresponding to no identifiable dip in the detected green RGB color value at a horizontal pixel position range of approximately 210-230 as depicted on the graph.

For purposes associated with this filtering step, digital filters (low pass filters and/or band pass filters) of various types and various degrees may be utilized in association with various embodiments of the present disclosure. The filtration step addresses the challenge of collecting usable values due the excessive amount of image noise. A graph of the collected values demonstrating unusable image noise is displayed on FIGS. 3A-3C. In such figures, many false "dips" in the RGB channel color value may be detected as evidenced by the variations in the intensity at a variety of horizontal pixel positions moving from left to right. In the context of the disclosure, the term "noise" may refer to random variations of amplitude and frequency superimposed on the desired signal. For illustration, if one applied a random noise generator and to a sine wave, the sine wave will comprise sharp spikes up and down at different frequencies, making the determination of where the sine wave begins and ends more complicated and possibly impossible. Such example demonstrates "noisy" spikes. These spikes, like those depicted on FIGS. 3A-3C, are made up of much higher frequency components added to the much lower frequency sine wave or result "dip." For example, even if a standard trend is determined, when you get to the sine wave peak at a horizontal axis location, it would be difficult to evaluate whether a point corresponds to a low spike, or a high spike, or a point in the middle, to provide an accurate measurement due to noise. This problem left unaddressed in the context of the present disclosure might result in inconsistent measurements. If the spikes can be smoothed out such that you only have tiny spikes, it is very consistent and easy to measure, and thus the data can be interpreted, measured and processed properly. Therefore, the filtering step as described herein is advantageous in association with an embodiment of the disclosure.

Figure 4A:
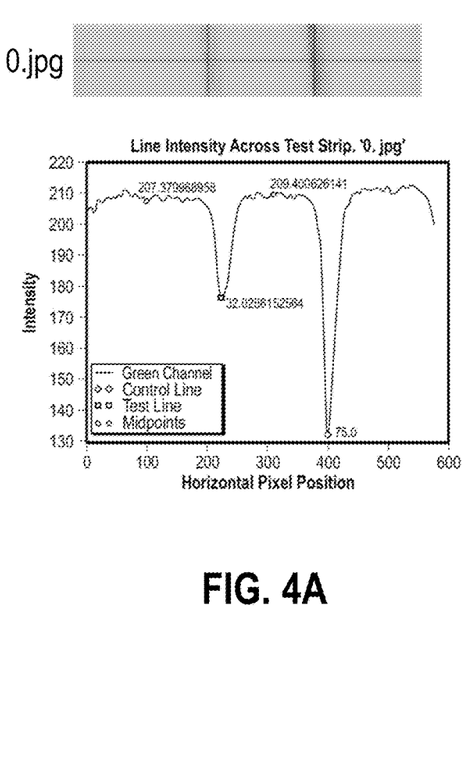
FIG. 4A depicts exemplary detected RGB channel color values following the application of a filter, optionally a digital low pass filter, detected at a plurality of horizontal pixel positions across the photographed diagnostic test following the application of a synthetic urine solution containing 0 ug/mL of a hormone or analyte amount (and correspondingly named 0.jpg) moving in a left to right direction. Note that the red associated with the test line is clearly visible at the location of the test line both on the photographed diagnostic test and as indicated on the graph, corresponding to a clearly identifiable dip in the detected green RGB color value at a horizontal pixel position range of approximately 210-230 as depicted on the graph.
Figure 4B:
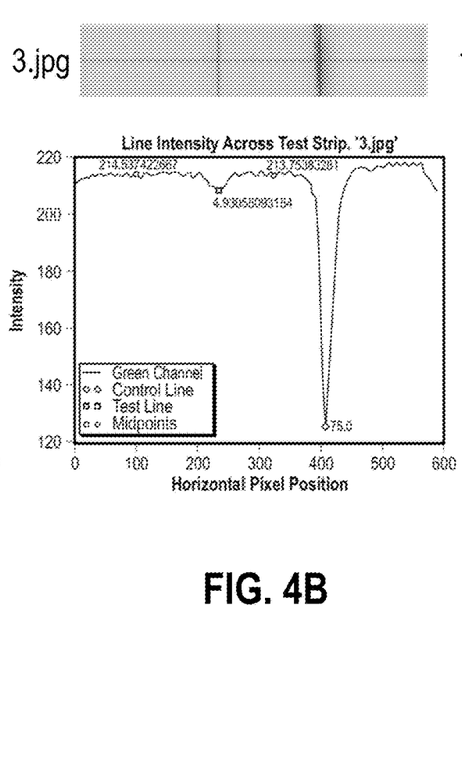
FIG. 4B depicts exemplary detected RGB channel color values following the application of a filter, optionally a digital low pass filter, detected at a plurality of horizontal pixel positions across the photographed diagnostic test following the application of a synthetic urine solution containing 3 ug/mL of a hormone or analyte amount (and correspondingly named 3.jpg) moving in a left to right direction. Note that the red associated with the test line is only slightly visible at the location of the test line both on the photographed diagnostic test and as indicated on the graph, corresponding to a only slightly identifiable dip in the detected green RGB color value at a horizontal pixel position range of approximately 210-230 as depicted on the graph.
Figure 4C:
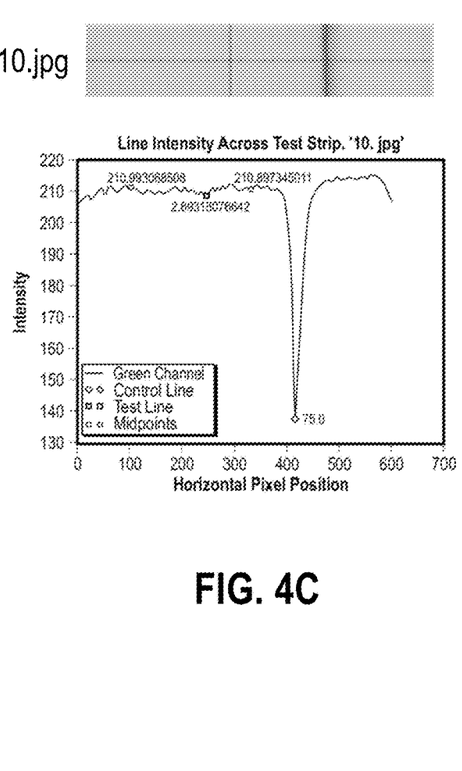
FIG. 4C depicts exemplary detected RGB channel color values following the application of a filter, optionally a digital low pass filter, detected at a plurality of horizontal pixel positions across the photographed diagnostic test following the application of a synthetic urine solution containing 10 ug/mL of a hormone or analyte amount (and correspondingly named 10.jpg) moving in a left to right direction. Note that the red associated with the test line is not visible at the location of the test line both on the photographed diagnostic test and as indicated on the graph, corresponding to no identifiable dip in the detected green RGB color value at a horizontal pixel position range of approximately 210-230 as depicted on the graph.

Low pass filtering (or band pass filter) does not accomplish averaging. The targeted noise corresponds with high frequency components superimposed on top of the lower frequency waveform of interest. Filtration attenuates the high frequency noise of the wave form sought and leaves the low frequency components of the waveform mostly unchanged. Thus, the sought "dips" in color value, associated with the results depicted by one or more test lines of a photographed diagnostic test, reflecting the low frequency waveform are more easily detected and evaluated, as depicted on the graphs of FIGS. 4A-4C.

5. Identifying the Location of Each Testing Line and the Control Line of the Photographed Diagnostic Test.

In the example of a diagnostic test comprising a single test line configured to provide a result for the concentration of PdG in an applied fluid, the deepest reduction, or "dip," in the RGB channel color value (associated with a color other than the predominant color associated with the label utilized within the diagnostic test) at a horizontal pixel position of a photograph of the diagnostic test or cropped area of the photograph of the diagnostic test generally correlates with the control line of the diagnostic test. In an alternative example, the deepest reduction, or "dip," in the RGB channel color value at a horizontal pixel position of a photograph of a diagnostic test or cropped area of the photograph of a diagnostic test can correlates with the control line if the testing line is negative or the testing line if the testing line is positive of the diagnostic test, in the case of a diagnostic test comprising a single test line configured to provide a result for the concentration of LH in an applied fluid.

In one example, the testing line is a distance measurable in pixels away from the location of the horizontal pixel position of the control line of the diagnostic test, where each pixel has a known dimension corresponding to a distance between a control line and test line of the photographed test, with the pixel normalization calculated as a result of a measurement in pixels between the horizontal positions of each of two detected reductions in RGB color value on a photographed diagnostic test or cropped area of a photographed diagnostic test, and then normalizing the measurement in pixels by applying the previously known physical distance between the control line and test line.

In an alternative embodiment, presuming the photograph of the strip is properly cropped, the testing region of the strip, which in an example is identified via machine learning in association with methods understood by those skilled in the art, may be divided in half horizontally. Following the horizontal division, which leads to the identification of a center line along the height of the center of the horizontal division, the deepest dip is then found on either side of the center line. For example, in an embodiment featuring a diagnostic test comprising a single testing line, when properly oriented and cropped, the deepest dip on the right side of the horizontal center of the photograph cropping corresponds to the control line of the diagnostic test and the deepest dip on the left side of the horizontal center of the photograph cropping corresponds to the testing line of the diagnostic test.

Thus, the system can engage in a step of identifying the location of the control line and each testing line depicted within a photographed diagnostic test or cropped area of the photograph of a diagnostic test by analysis of the RGB color channel value or average of the RGB color channel values collected at each horizontal pixel position of the photograph of a diagnostic test or cropped area of the photograph of a diagnostic test.

Example Comprising Diagnostic Test Comprising a Single Test Line

In an example featuring a photograph of a diagnostic test comprising a single test line, the location of the test line is determined by identifying the horizontal pixel position that has the most "dip" (the term "dip" referring to a decrease in RGB color channel value or average RGB color channel value from a midpoint value). Optionally, the dip occurs at horizontal pixel position above a pre-determined number of pixels away in either a left or a right direction on the photograph of a diagnostic test or cropped area of the photograph of a diagnostic test. On each side of the dip, it is possible to identify the flat region, labeled as one or more "midpoints" on the various graphs associated with FIGS. 4A-4C and 5A-5C, corresponding to the white region on the photographed diagnostic test located between the control line and one test line (or in an alternative embodiment, a first test line and another test line). From this information the amplitude of the dip is measured, an average is calculated and then quantified to determine a numerical representation of how deep the dip goes relative to that average in terms of RGB color channel values. That depth is a value of pixel intensity drop for that RGB channel color. In a preferred embodiment, the RGB green color channel value dip magnitude of a photographed diagnostic test closely corresponds to the red intensity present in the test line of the photographed diagnostic test.

Example Comprising Diagnostic Test Comprising Multiple Test Lines

In an example featuring a photograph of a diagnostic test comprising multiple testing lines, the outermost dips are first identified, corresponding to a control line and one of the plurality of testing lines on the diagnostic test. The distance between the outermost testing lines (optionally in pixels) is then determined in the photograph and then correlated to a known physical distance associated with known characteristics of the diagnostic test. The location of additional testing lines on the photographed diagnostic test may then be approximated by normalizing the pixel distance to the known physical distance and applying the same normalization to determine the pixel distance between at least one of the control line and/or testing line and one or a plurality of additional testing lines on the photographed diagnostic test, when the physical distance of the same is known. In an embodiment, the photographed diagnostic test is configured such that the control line is the right-most line within the testing window and a test line configured to provide an indication of the concentration of luteinizing hormone (LH) in an applied fluid is the left-most line within the testing window. Further in such embodiment, the known physical dimensions of the diagnostic test are normalized into pixels to determine the approximate location within the photograph of a test line configured to provide an indication of the concentration of estradiol (E1G) in an applied fluid at a distance to the left of the control line and the approximate location of a test line configured to provide an indication of the concentration of pregnanediol glucuronide (PdG) in an applied fluid at a distance to the right of the test line configured to provide an indication of the concentration of luteinizing hormone (LH) in an applied fluid. In an embodiment, the known physical dimensions of the diagnostic test are also be normalized to generate an error message in association with an application utilizing the steps described herein if the pixel distance between a control line and a test line, or between test lines, is too low. In an embodiment, following the detection of a quantity of lines other than the expected quantity of lines based upon knowledge of the configuration of the diagnostic test may generate an error message in association with an application utilizing the steps described herein.

In an example, where the length of the photograph or the cropped area of the photograph is known and knowing the approximate length of the photographed diagnostic test or area is known, that information is used to determine how far from the control line that the test line is located. In an exemplary embodiment this comprises identifying the absolute length of the diagnostic test or the cropped area of the diagnostic test, and then identifying the different corners of the diagnostic test or the cropped area of the diagnostic test due to the different resolutions of the different corners, then converting the length into the length of each pixel, and then performing the appropriate unit normalizations and associated measurements to determine the location of each testing line on the photograph of the diagnostic test or cropped area of the photograph of the diagnostic test. In various embodiments, machine learning is utilized to identify the length and/or the cropped area of the diagnostic test and to ensure proper orientation by, for example, algorithmically comparing a photographed image of a diagnostic test to one or more previously mapped photographed images (with mapping corresponding to the area to be cropped) of diagnostic test(s) and extrapolating the area of the presently photographed diagnostic test to crop and re-orient as necessary, in association with methods as understood by those skilled in the art.

An embodiment comprises a "Sensitivity Knob." As referred to herein, the Sensitivity Knob is a coefficient that determines how much of a dip correlates to a significant result. The sensitivity knob is a RGB channel intensity value that stems from the expectation of the distance from the variation in intensity up and down to be a certain distance (in pixels, of horizontal pixel position) apart. The intensity number stems from the recognition of the significance of the magnitude of the dip as relates to the discovery of a result on a diagnostic test. The Sensitivity Knob in an embodiment is used to determine if a dip occurs after averaging and filtering. One example method of its functionality is as follows:

In an example, the method examines the green RGB intensity value 20 pixels into the width of the image, and sets this as the center value for the purpose of comparison to surrounding values. Then, its intensity is compared to the intensity of pixels on either side of this value at fixed distances. The center is then moved one pixel at a time, to make this comparison across the entire image. If the difference at any given center is greater than the sensitivity value, then a dip has occurred at the center location. In this case, there can be multiple findings, of which only one is the correct dip location. In an example, this correct dip location is determined later by a sorting function. There can be other methods to determine a dip, but in this context, the idea is the same. In the context of the present disclosure the Sensitivity Knob cannot be set too low, otherwise noise will trigger a result. Thus, in a preferred embodiment, it is preferable to set the Sensitivity Knob so that typically only the dips associated with results of the diagnostic test are identified. To configure the Sensitivity Knob, trial and error is necessary to determine a value that does not in the vast majority of cases allow noise to be interpreted as a result of the testing line. In a preferred embodiment, the Sensitivity Knob is set to a value that gives good results.

In the context of a preferred embodiment of the present disclosure, in an example of a diagnostic test where the absence of color at the location of a testing line indicates a positive result, if the sensitivity knob picks up nothing, then the interpreted result of the diagnostic test is positive. It is not desirable to have a Sensitivity Knob that is sensitive enough such that if a dip is detected due to noise that a positive result is not indicated even when there is no observable color within a testing zone. Further, in an example, very slight color in a testing zone may still correlate to a very low hormone or analyte level indicative of a positive result. In such example and in the context of the present disclosure, it is desirable to set the Sensitivity Knob such that a slight dip corresponds to a hormone level still resulting in a positive interpretation.

6. Normalizing the Depth of the Control Line.

The depth of the control line will differ slightly in association with each photographed diagnostic test. This stems from a variety of factors including lighting, brightness, camera color temperature, white level balance, etc. that require normalization to allow for the accurate detection of a result. However, as the control line intensity changes, the test line intensity will accordingly change. The control line of a similarly configured diagnostic test should remain generally constant from diagnostic test to diagnostic test following the application of fluids regardless of the concentration of hormones and/or analytes present in such fluids. Thus, the system can normalize each RGB channel color value observed at each horizontal pixel position to the RGB channel color value of the control line. In varying embodiments, the normalizing step is performed on a photograph of a diagnostic test comprising a single testing zone or a photograph of a diagnostic test comprising a plurality of testing zones.

To perform the step of normalizing the depth of the control line in association with a preferred embodiment, the following steps are performed:

1. Determining the normalization factor. In an embodiment, the normalization factor is the coefficient necessary to multiply the reference line by to attain the sum representing the fixed depth value. For example, when desirable to normalize the control line to 100, the detected value at the control line horizontal pixel position is multiplied by whatever factor (the "normalization factor") needed to reach a value (a fixed depth value) of 100. In a preferred embodiment, the fixed depth value is set to 75, as a typical control line dip in a preferred embodiment is approximately 75 RGB green channel color value units.

For example, in such preferred embodiment, if the depth is 50, then one would need to multiply by a normalization factor of 1.5 to normalize to 75, or if the depth is 100, then one would need to multiply by a normalization factor of 0.75 to normalize to 75. Then one would apply the relevant normalization factor to the test line to arrive at the normalized RGB green channel color value for each test line present on the subject diagnostic test. The normalized RGB green channel color value for the test line then may be cross-referenced to a normalized hormone or analyte level, optionally determined in conjunction with the calibration step as described herein, corresponding to the normalized value for the test line. The resulting data may yield a hormone or analyte level present in the fluid applied to the relevant diagnostic test as determined from a curve fit equation, optionally as determined by plots generated from calibration sets of photographed diagnostic tests following the application of fluid samples each with a fixed concentration of a hormone and/or an analyte.

2. Multiplying each of the values collected at each of the horizontal pixel position by the normalization factor. In an embodiment, the value at each horizontal pixel position is an average of multiple values collected along the vertical axis at the horizontal pixel position. In varying embodiments, each of the values associated the horizontal pixel position corresponding to each test line are multiplied by the normalization factor in particular. The normalized test line value is determined in association with the product of the normalization factor and the detected RGB channel color value at the horizontal pixel position associated with the test line, for example as indicated on FIG. 5A.

In an example, this normalization step in the context of the present disclosure addresses the issue that differing lighting conditions, cameras, shadows, color temperatures, etc. can cause the amplitudes of the RGB channel color values to vary, though in a consistent basis across the horizontal length of a photographed diagnostic test or cropped area of a photographed diagnostic test. In an example, the identification of an unacceptable lighting condition, shadow, and/or color temperature may lead a determination that the photograph of the test is invalid, and the normalization step is then replaced by an error message prompting a user to instead attempt to recapture a photograph of the test in a changed environment without the unacceptable lighting condition, shadow, and/or color temperature. The determination of whether the lighting condition, shadow, and/or color temperature is unacceptable optionally occurs as a result of comparing multiple midpoint values for consistency; evaluating the brightness, color level and/or consistency of color levels within the white area of a photographed diagnostic test; and/or assessing whether the dip measurements fall within a predetermined expected range. In an embodiment, following the detection of a shadow at the edge of a diagnostic test based upon knowledge of the configuration of the diagnostic test and its expected appearance in a photograph may generate an error message in association with an application utilizing the steps described herein.

7. Calibrating to Determine a Hormone or Analyte Level Corresponding to a Color Value of a Test Line.

In various embodiments, it is advantageous to evaluate a number of fluid samples, each sample containing a predetermined concentration of hormone or analyte. Each fluid sample containing a predetermined concentration of at least one particular hormone or analyte is tested with the diagnostic test intended for use in some embodiments. A photograph of the diagnostic test or cropped area of the photograph of the diagnostic test is evaluated to determine the RGB channel color value of each test line in following the application of a fluid sample containing a predetermined concentration of at least one particular hormone or analyte to the diagnostic test. The RGB channel color value of the testing line relevant to each predetermined concentration of hormone or analyte may therefore be determined and associating the predetermined concentration of a hormone or analyte in the fluid with the detected color value of the testing line relevant to the hormone or analyte.

In various embodiments, the RGB channel color value is normalized, and/or the RGB channel color value is fixed in a constant condition to ensure that the variables that otherwise may impact the detected RGB color value associated with each test line remain consistent from test to test. The RGB channel color value of each test line depicted on the photograph of the diagnostic test is then associated with the known concentration of hormone and/or analyte with each photographed diagnostic test or cropped area of the photograph of the diagnostic test. In varying embodiments, the calibrating step is performed on a photograph of a diagnostic test comprising a single testing zone or a photograph of a diagnostic test comprising a plurality of testing zones.

In a typical case, the intensity of the pigmentation relative to hormone or analyte concentration in an applied fluid can generally be curve fitted to a graph of a mathematical function. In such manner, each color value can be approximated to a hormone or analyte concentration. The calibration might change following a change in the characteristics of the diagnostic test. In a preferred embodiment, the calibration step is performed in association with a plurality of diagnostic tests, each applied to a differing hormone or analyte concentrations, and each diagnostic test of a similar configuration and of similar characteristics. If the sensitivity of the diagnostic test is changed, for instance, where the amount of pigmentation per unit of hormone and/or analyte changes, the relationship may likewise change. In the context of a preferred embodiment to perform consistently, the diagnostic test must be photographed at a consistent time period from the application of a fluid containing a hormone or analyte subject to evaluation. Thus, in an embodiment, the calibration step further comprises photographing each diagnostic test during calibration at a consistent time period from the application of a fluid containing a hormone or analyte subject to evaluation. In various embodiments, the environmental conditions of each photographed diagnostic test to obtain the calibration, such as lighting and distance between the camera and each photographed diagnostic test, are held constant to minimize the impact of environmental factors. Thus, in an embodiment, the calibration step further comprises holding constant the environmental conditions of each photographed diagnostic test throughout the calibration to minimize the impact of environmental factors. In various embodiments, the equation approximating the relationship of RGB channel color value to concentration of hormone and/or analyte in an applied fluid may be a function, a piecemeal approximation or a lookup table. In varying embodiments, any method of corresponding an output level with intensity can be used.

Figure 8:
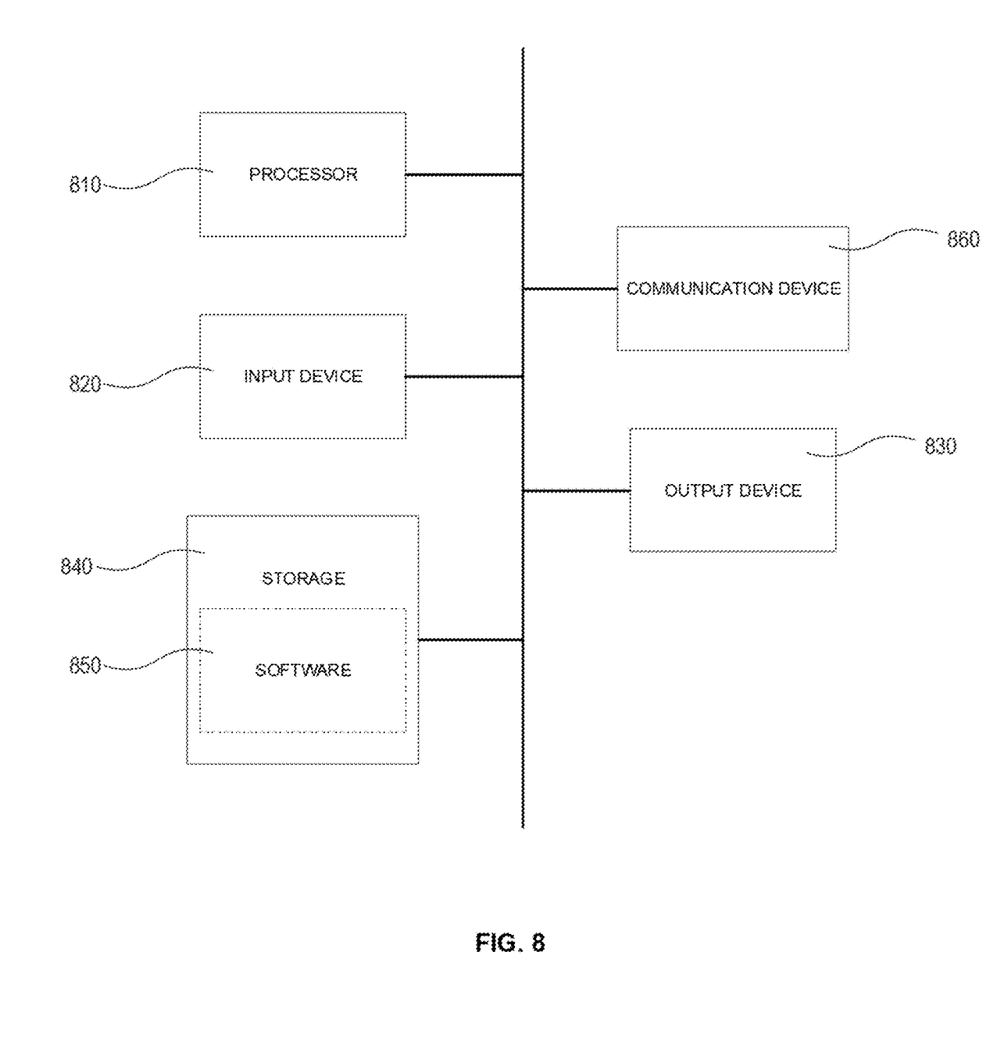
FIG. 8 illustrates an exemplary electronic device, in accordance with some embodiments.

The operations described herein are optionally implemented by components depicted in FIG. 8. FIG. 8 illustrates an example of a computing device in accordance with one embodiment. Device 800 can be a host computer connected to a network. Device 800 can be a client computer or a server. As shown in FIG. 8, device 800 can be any suitable type of microprocessor-based device, such as a personal computer, workstation, server or handheld computing device (portable electronic device) such as a phone or tablet. The device can include, for example, one or more of processor 810, input device 820, output device 830, storage 840, and communication device 860. Input device 820 and output device 830 can generally correspond to those described above, and can either be connectable or integrated with the computer.

Input device 820 can be any suitable device that provides input, such as a touch screen, keyboard or keypad, mouse, or voice-recognition device. Output device 830 can be any suitable device that provides output, such as a touch screen, haptics device, or speaker.

Storage 840 can be any suitable device that provides storage, such as an electrical, magnetic or optical memory including a RAM, cache, hard drive, or removable storage disk. Communication device 860 can include any suitable device capable of transmitting and receiving signals over a network, such as a network interface chip or device. The components of the computer can be connected in any suitable manner, such as via a physical bus or wirelessly.

Software 850, which can be stored in storage 840 and executed by processor 810, can include, for example, the programming that embodies the functionality of the present disclosure (e.g., as embodied in the devices as described above).

Software 850 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 840, that can contain or store programming for use by or in connection with an instruction execution system, apparatus, or device.

Software 850 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 800 can implement any operating system suitable for operating on the network. Software 850 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

The methods disclosed herein comprise one or more steps or actions for achieving the described method. The method steps and/or actions may be interchanged with one another without departing from the scope of the claims. The order and/or use of specific steps and/or actions may be modified without departing from the scope of the claims.

It is to be understood that the claims are not limited to the precise configuration and components illustrated above. Various modifications, changes and variations may be made in the arrangement, operation and details of the methods and apparatus described above without departing from the scope of the disclosure.

While the foregoing is directed to aspects of the present disclosure, other and further aspects of the disclosure may be devised without departing from the basic scope thereof.

What is claimed is:

1. A method of interpreting results indicated on a photographed diagnostic test, comprising:

sweeping the photographed diagnostic test, or cropped area of the photographed diagnostic test;
calculating an average of color channel values from a plurality of vertical pixel positions at a particular horizontal pixel position of the photographed diagnostic test or cropped area of the photographed diagnostic test; and
repeating the calculating the average step to obtain the average of color channel values from a plurality of vertical pixel positions for each of a plurality of horizontal pixel positions;
creating a vector of color values including the color values obtained from the plurality of horizontal pixel positions on the photographed diagnostic test or cropped area of the photographed diagnostic test;
identifying the location of the control line and each testing line depicted within the photographed diagnostic test; and
calibrating to determine a hormone or analyte level corresponding to a color value of a test line.

2. The method of claim 1, further comprising: filtering the photographed diagnostic test or the cropped area of the photographed diagnostic test.

3. The method of claim 1, further comprising: normalizing the depth of the control line.

4. The method of claim 3, wherein the normalizing further comprises:
determining the normalization factor; and
multiplying each of the values collected at each of the horizontal pixel positions by the normalization factor.

5. The method of claim 1, wherein the calibration further comprises:
holding constant the environmental conditions of each photographed diagnostic test throughout the calibration to minimize the impact of environmental factors.

6. The method of claim 1, wherein the calibration further comprises:
photographing each diagnostic test during calibration at a consistent time period from the application of a fluid containing a hormone or analyte subject to evaluation.

7. The method of claim 1, wherein the diagnostic test comprises a single testing zone configured to indicate the concentration of a hormone or analyte in a fluid applied to the diagnostic test.

8. The method of claim 1, wherein the diagnostic test comprises a plurality of testing zones each configured to indicate the concentration of a discrete hormone or analyte in a fluid applied to the diagnostic test.

9. The method of claim 1, wherein the color values of a RGB channel other than the predominant color are expected on at least one test line of the photographed diagnostic test.

10. The method of claim 1, further comprising: converting a color image to a grayscale image prior to the creating a vector of color values step.

11. The method of claim 1, further comprising: converting a grayscale image to a RGB image.

12. A system of interpreting results indicated on a photographed diagnostic test, comprising:
one or more processors;
a memory; and
one or more programs, wherein the one or more programs are stored in the memory and configured to be executed by the one or more processors, the one or more programs including instructions for:
sweeping the photographed diagnostic test, or cropped area of the photographed diagnostic test;
calculating an average of color channel values from a plurality of vertical pixel positions at a particular horizontal pixel position of the photographed diagnostic test or cropped area of the photographed diagnostic test; and
repeating the calculating the average step to obtain the average of color channel values from a plurality of vertical pixel positions for each of a plurality of horizontal pixel positions;
creating a vector of color values including the color values obtained from the plurality of horizontal pixel positions on the photographed diagnostic test or cropped area of the photographed diagnostic test;
identifying the location of the control line and each testing line depicted within the photographed diagnostic test; and
calibrating to determine a hormone or analyte level corresponding to a color value of a test line.

13. A non-transitory computer-readable storage medium storing one or more programs, the one or more programs comprising instructions, which when executed by one or more processors of an electronic device having a display, cause the electronic device to:
sweep the photographed diagnostic test, or cropped area of the photographed diagnostic test;
calculate an average of color channel values from a plurality of vertical pixel positions at a particular horizontal pixel position of the photographed diagnostic test or cropped area of the photographed diagnostic test; and
repeat the calculating the average step to obtain the average of color channel values from a plurality of vertical pixel positions for each of a plurality of horizontal pixel positions;
create a vector of color values including the color values obtained from the plurality of horizontal pixel positions on the photographed diagnostic test or cropped area of the photographed diagnostic test;
identify the location of the control line and each testing line depicted within the photographed diagnostic test; and
calibrate to determine a hormone or analyte level corresponding to a color value of a test line.

* * * * *